(12) United States Patent
Katzman et al.

(10) Patent No.: US 6,186,958 B1
(45) Date of Patent: Feb. 13, 2001

(54) BREATH TEST ANALYZER

(75) Inventors: Daniel E. Katzman, Kfar Bin Nun; Ephraim Carlebach, Ra'anana, both of (IL)

(73) Assignee: Oridion Medical, Jerusalem (IL)

(*) Notice: Under 35 U.S.C. 154(b), the term of this patent shall be extended for 0 days.

(21) Appl. No.: 09/151,135

(22) Filed: Sep. 10, 1998

Related U.S. Application Data (63) Continuation-in-part of application No. 08/805,415, filed on Feb. 26, 1997, now Pat. No. 6,067,989.

(51) Int. Cl.$^7$ ..................................................... A61B 5/08
(52) U.S. Cl. ........................ 600/532; 600/529; 436/811; 424/84; 128/898
(58) Field of Search ..................................... 600/529–538, 600/500–504; 128/897–899; 436/181, 811; 422/83–84; 250/339.03, 345, 343–344

(56) References Cited

U.S. PATENT DOCUMENTS

| | | |
|---|---|---|
| Re. 33,493 | 12/1990 | Lee et al. . |
| 4,684,805 | 8/1987 | Lee et al. . |
| 4,830,010 * | 5/1989 | Marshall ............................ 600/529 |
| 5,063,275 | 11/1991 | Rosenfeld et al. . |
| 5,077,469 | 12/1991 | Fabinski et al. . |
| 5,317,156 | 5/1994 | Cooper et al. . |
| 5,394,236 | 2/1995 | Murnick . |
| 5,640,014 | 6/1997 | Sauke et al. . |
| 5,848,975 * | 12/1998 | Phillips ................................ 600/532 |
| 5,944,670 * | 8/1999 | Katzman ............................. 600/529 |

FOREIGN PATENT DOCUMENTS

| | | |
|---|---|---|
| 0 204 438 | 10/1986 | (EP) . |
| 0 206 625 | 8/1988 | (EP) . |
| 0 206 626 | 8/1988 | (EP) . |
| 0 584 897 | 3/1994 | (EP) ............................. G01N/21/37 |
| 0 672 383 A2 | 9/1995 | (EP) . |
| WO 95/11672 | 5/1995 | (WO) . |
| WO 97/14029 | 4/1997 | (WO) ............................ G01N/21/35 |

OTHER PUBLICATIONS

Barrett, L.J., *ASM Las Vegas 1994*, "Evaluation of Pyloriscreen Assay for Detection of *H. pylori* Infection vs. Culture, Histology, CLOtest and 14C Urea Breath Test", 1994.

Bielanski, W., et al. *Journal of Physiology and Pharmacology*, "Microdose 14C–Urea Breath Test in Detection of *Helicobacter pylori*", vol. 47, No. 1, pp. 91–100, 1996.

Bloch, K., *The Journal of Biological Chemistry*, "The Metabolism of /(+)–Arginine in the Rat", vol. 165, No. 2, pp. 469–484, 1946.

(List continued on next page.)

*Primary Examiner*—Cary O'Connor
*Assistant Examiner*—Michael Astorino
(74) *Attorney, Agent, or Firm*—Morgan & Finnegan (57) ABSTRACT

A breath test analyzer, which analyzes exhaled breaths of a patient for isotope labeled products generated in the patient's body after ingestion by the patient of an isotope labeled substance, where the presence of these isotope labeled products provide an indication of a medical condition in the patient. The analyzer uses a very sensitive infra-red spectrophotometer, which enables it to continuously collect and analyze multiple samples of the patient's breath, and process the outputs in real time, while the patient is still connected to the analyzer, such that a definitive result is obtained within a short time, such as the order of a few minutes. The breath test analyzer is sufficiently small that it can be easily accomodated in the office of a physician. The breath test analyzer can be utilized for a number of diagnostic breath tests, according to the isotope labeled substance ingested by the patient and the gases detected in the patient's breath.

53 Claims, 6 Drawing Sheets

OTHER PUBLICATIONS

Caldwell, S.H., et al. *Clinical Research*, "How Common is *Campylobacter pylori* in Persons without Dyspepsia?", vol. 37, No. 1, 1989.

Caldwell, S.H., et al. *The American Journal of Medicine*, "Possible Role of *Campylobacter pylori* in Idiopathic Hyperammonemia", vol. 87, pp. 249–250, 1989.

Caldwell, S.H., et al. *Drug Therapy*, "*Campylobacter pylori* and Peptic Disease" vol. 19 No. 5, pp. 92–106, 1989.

DeCross, A.J., et al. *Journal of Clinical Microbiology*, "Metronidazole Susceptibility Testing for *Helicobacter pylori* Comparison of Disk, Broth, and Agar Dilution Methods and Their Clinical Relevance", vol. 31, No. 8, pp. 1971–1974, 1993.

Combs, M.J., et al. *Gastroenterology*, vol. 108, No. 4, 1995.

Combs, M.J., et al. *JNM*, "Dosimetry and Reproducibility of a Capsule–bases C–14 Urea Breath Test", vol. 36, No. 5, 1995.

Cutler, A.F., et al. *Gastroenterology*, "Accuracy of Invasive and Noninvasive Test to Diagnose *Helicobacter pylori* Infection" vol. 109, No. 1, pp. 136–141, 1995.

Dye, K.R., et al. *Digestive Diseases and Sciences*, "Ultrastructure of Another Spiral Organism Associated with Human Gastritis", vol. 34, No. 11, pp. 1787–1791, 1989.

Evans, D.J., *Gastroenterology*, "A Sensitive and Specific Serologic Test for Detection of *Campylobacter pylori* Infection", vol. 96, No. 4, pp. 1004–1008, 1989.

Frierson, H.F. Jr., et al. *Laboratory Investigation*, "A Spiral Bacterium Distinct from *Campylobacter pylori* that Causes Gastritis in Humans", vol. 60, No. 1, 1989.

Godle, H., et al. *Nuclear Science Abstracts*, vol. 4, No. 18, p. 806, 1950.

Graham, D.Y., et al. *The American Journal of Gastroenterology*, "*Campylobacter pyloridis* Gastritis: The Past, the Present, and Speculations about the Future", vol. 82, No. 4, pp. 283–286, 1987.

Graham, D.Y., et al. *The Lancet*, "*Campylobacter pylori* Detected Noninvasively by the $^{13}$C–Urea Breath Test", vol. I, pp. 1174–1177, 1987.

Graham, D.Y., et al. *Scandinavian Journal of Gastroenterology*, "Epidemiology of *Campylobacter pylori* Infection: Ethnic Considerations", pp. 9–13, 1988.

Graham, D.Y., et at. *The Journal of Infectious Diseases*, "Effect of Age on the Frequency of Active *Campylobacter pylori* Infection Diagnosed by the [$^{13}$C]–Urea Breath Test in Normal Subjects and Patients with Peptic Ulcer Disease", vol. 157, No. 4, pp. 777–780, 1988.

Graham, D.Y., et al. *The American Journal of Gastroenterology*, "In Vivo Susceptibility of *Campylobacter pylori*", vol. 84, No. 3, pp. 233–238, 1989.

Kerr, D., et al. *The Lancet*, "Adrenaline Response to Hypoglycemia and Insulin Species", vol. I, p. 836, 1989.

Klein, P.D., *Stable Isotopes in Nutrition Research*, "Clinical Applications of $^{13}CO_2$ Measurements" pp. 2698–2701, 1982.

Klein P.D., et al. *The Lancet*, "Water Source as RiskFactor For *Helicobacter pylori* infection in Peruvian Children" vol. 337, pp. 1503–1506, 1991.

Klein, P.D., et al. *The American Journal of Gastroenterology*, "Noninvasive Detection of *Helicobacter pylori* Infection in Clinical Practice: The $^{13}$C Urea Breath Test", vol. 91, No. 4, pp. 690–694, 1996.

Kornberg, H.L., et al. *Ile Congres International De Biochimie*, "The Metabolism of Urea in the Cat", 1959.

Langham, W.H., *The Journal of Biological Chemistry*, "Studies on the Metabolism of Radioactive Nicotinic Acid and Nicotinamide in Mice", vol. 176, No. 1, pp. 249–257, 1948.

Leifer, E., et al. *Science*, "Metabolism of $C^{14}$–labeled Urea", vol. 108, p. 748, 1948.

Marshall, B.J., et al. *The Lancet*, "Unidentified Curved Bacilli in the Stomach of Patients with Gastritis and Peptic Ulceration", vol. I, pp. 1311–1315, 1984.

Marshall, B.J., et al. *The Medical Journal of Australia*, "Pyloric Campylobacter Infection and Gastroduodenal disease", vol. 142, pp. 439–444, 1985.

Marshall, B.J., *The Journal of Infectious Diseases*, "*Campylobacter pyloridis* and Gastritis", vol. 153, No. 4, pp. 650–657, 1986.

Marshall, B.J., et al. *Digestive Diseases and Sciences*, "CLOtest A Rapid Urease Test for the Detection of *Campylobacter pyloridis* Infection in Gastric Mucosal Biopsies" vol. 31, No. 10, 1986.

Marshall, B.J., et al. *The American Journal of Gastroenterology*, "Rapid Urease Test in the Management of *Campylobacter pyloridis*–Associated Gastritis", vol. 82, No. 3, pp. 200–210, 1987.

Marshall, B.J., et al. *Gastroenterology*, "Fifteen Minute Urea–C14 Breath Test for the Diagnosis of Campylobacter Associated Gastritis", vol. 92, No. 5, pp. 1517–1518, 1987.

Marshall, B.J., et al. *The Journal of Nuclear Medicine*, "Sensitive, Specificity and Reproducibility of the C–14 Urea Breath Test: Evaluation in Patients with *C. pylori*", vol. 29, No. 5, p. 790, 1988.

Marshall, B.J., et al *Clinical Research*, vol. 36, No. 1, 1988.

Marshall, B.J., et al *The Journal of Nuclear Medicine*, "Carbon–14 Urea Breath Test for the Diagnosis of *Campylobacter pylori* Associated Gastritis" vol. 29, No. 1, 1988.

Marshall, B.J., et al. *Scandinavian Journal of Gastroenterology*, "The *Campylobacter pylori* Story", vol. 23, Supp. 146, 1988.

Marshall, B.J., et al. *The American Journal of Gastroenterology*, "Is CLOTEST Alone Adequate to Diagnose *Campylobacter pylori*", vol. 83, No. 83, 1988.

Marshall, B.J., et al. *Gastroenterology*, "Comparison of 14C–Urea Breath Test, Microbiology and Histologoy for the Diagnosis of *Campylobacter pylori*" vol. 94, No. 5, 1988.

Marshall, B.J., *The American Journal of Gastroenterology*, "Should We Now, Routinely, Be Examining Gastric Biopsies for *Campylobacter pylori*?", vol. 83, No. 5, pp. 479–481, 1988.

Marshall, B.J., et al. *The Journal of the American Medical Association*, "*Campylobacter pylori*: Diagnosis and Treatment", vol. 260, No. 19, 1988.

Marshall, B.J., *The Medical Journal of Australia*, "*Campylobacter pylori* infection: diagnosis and therapy", vol. 151, pp. 426–427, 1989.

Marshall, B.J., *Gastroenterologie Clinique et Biologique*, "Experimental models in vivo for *Campylobacter pylori*", vol. 13, 1989.

Marshall, B.J., et al. *Gastroenterology*, "Microdose, Capsule–Based, 14C–Urea Breath Test For *H.pylori*", vol. 96, No. 5, p. 321, 1989.

Marshall, B.J., et al. *Gastroenterology*, "Urea Protect Helicobacter (*Campylobacter*) *pylori* from the Bactericidal Effect of Acid", vol. 99, No. 3, pp. 698–702, 1990.

Marshall, B.J., et al. *Gastroenterology*, vol. 98, No. 5, p. 83, 1990.

Marshall, B.J., et al. *Gastroenterology*, "A Microdose, Capsule–Based $^{14}$C–Urea Breath Test for *H.pylori*", p. 118, 1991.

Marshall, B.J., et al. *The American Journal of Gastroenterology*, "A 20–Minute Breath Test for *Helicobacter pylori*", vol. 86, No. 4, pp. 438–445, 1991.

Marshall, B.J., *The Gastroenterologist*, "*Helicobacter pylori*: A Primer for 1994", vol. 1, No. 4, pp. 242–247, 1993.

Marshall, B.J., *The American Journal of Gastroenterology*, "*Helicobacter pylori*", vol. 89, No. 8, pp. 116–128, 1994.

*NIH Consensus Statement*, vol. 12, No. 1, 1994.

Opekun, A.R., et al. *Digestive Diseases and Sciences*, "[$^{13}$C] Aminopyrine Breath Test Detects Altered Liver Metabolism Caused by Low–Dose Oral Contraceptives", vol. 40, No. 11, pp. 2417–2422, 1995.

Roth, L.J., et al *The Journal of Biological Chemistry*, "Studies on the Metabolism of Radioactive Nicotinic Acid and Nicotinamide in Mice", pp. 249–257, 1948.

Spencer, P.S., et al *The Lancet*, "Motorneurone Disease on Guam: Possible Role of a Food Neurotoxin", pp. 965–966, 1986.

Stubbs, J.B., et al *JNM*, "Radiation Dose Estimates for the Carbon–14–Labeled Urea Breath Test" vol. 34, No. 5, pp. 821–825, 1993.

Sue, M., et al. *Gastroenterology*, "Comparison of Two Treatment Strategies for the Eradication of *H. pylori* Utilizing a Screening Antibody Serum Blot Test and Confirmatory C–14 Breath Test", vol. 110, No. 4, p. 266, 1996.

Warren, J.R., *The Lancet*, "Unidentified Curved Bacilli on Gastric Epithelium in Active Chronic Gastritis", pp. 1273–1275, 1983.

Watkins, J.B., *The Journal of Laboratory and Clinical Medicine*, "$^{13}$C–trioctanoin: a Nonradioactive Breath Test to Detect Fat Malabsorption" vol. 90, No. 3, pp. 422–430, 1977

*The World Health Report 1996*, "Infectious Diseases and Cancer" p. 59, 1996.

Klein et al., *The American Journal of Gastorenterology*, vol. 88, pp. 1865–1869, 1993.

Koletzko et al., *The Lancet* 345:961–2, 1995.

Kornberg et al., *Physiological Reviews*, vol. 35, pp. 169–177, 1955.

Peura, D.A. et al., *American Journal of Gastroenterology*, 91:233–238, 1996.

Von Korff, W., et al., *The American Journal of Physiology*, vol. 165, pp. 688–694, 1951.

\* cited by examiner

BREATH TEST ANALYZER

CROSS REFERENCE TO RELATED APPLICATION

This is a continuation-in-part of commonly-assigned U.S. patent application Ser. No. 08/805,415, filed Feb. 26, 1997 now U.S. Pat. No. 6,067,989.

FIELD OF THE INVENTION

The invention relates to the field of analyzers of the breath of patients to detect the gastric by-products of various diseases and infections.

BACKGROUND OF THE INVENTION

Since the early 1950's, it has been known that the presence of bacterial organisms in the gastro-intestinal tract is accompanied by a high concentration of urease, which hydrolyses urea to form carbon dioxide and ammonia. These gases are detected in the subject's blood stream and ultimately, in the subject's breath, if he had been administered isotopically labeled urea. Such early results appear in reviews published by R. W. VonKorff et al. in Am. J. Physiol., Vol. 165, pp. 688–694, 1951, and by H. L. Kornberg and R. E. Davies in Physiol. Rev., Vol. 35, pp. 169–177, 1955.

Since these early experiments, it has been found that there exist, in addition to the bacterial infections initially studied, a significant number of medical conditions associated with disorders of the gastro-intestinal tract or metabolic or organ malfunctions, which are capable of detection by means of such simple breath tests. These breath tests are based on the ingestion of an isotopically labeled sample, which is cleaved by the specific bacteria or enzymic action being sought, or as a result of the metabolic function being tested, to produce labeled gaseous by-products. These by-products are absorbed in the blood stream, and are exhaled in the patient's breath, where they are detected by means of external instrumentation.

Though the early experiments were performed using the radioactive carbon-14 atom, the most commonly used atom in such test procedures today is the carbon-13 atom, which is a stable, non-radioactive isotope, present in a proportion of about 1.1% of naturally occurring carbon. The labeled substance contains the functional compound to be used in the test, with almost all of its $^{12}C$ atoms replaced by $^{13}C$ atoms. Enrichments of up to 99% of $^{13}C$ are typically used. This compound is cleaved enzymatically under the specific conditions being tested for, either during gastric absorption, or during gastro-intestinal transit, or during its metabolisation in other organs of the body. The cleavage product produced is $^{13}CO_2$, which is absorbed in the bloodstream and exhaled in the patient's breath together with the $CO_2$ naturally present. The breath sample is then analyzed, usually in a mass spectrometer or a non-dispersive infra-red spectrometer. The increased presence of $^{13}CO_2$ is determined, as compared with the expected 1.1% of total $CO_2$ in healthy patient's breath, resulting from the metabolism of carbon compounds with the naturally occurring level of approximately 1.1% of carbon-13.

Though carbon-13 is the most commonly used isotopic replacement atom in such breath tests, other atoms which have been used include nitrogen-15 and oxygen-18. In addition, carbon-14 is still used in some procedures, but being radioactive, there are severe disadvantages both to its ingestion by the patient, and because of the storage, handling and disposal precautions required at the test site.

There are an increasing number of metabolic disorders, bacterial infections and organ malfunctions which can be diagnosed using such labeled substances for enabling breath tests. New applications are being proposed continuously, but among the more common currently in use are:

(a) The detection of *Helicobacter pylori* infections in the gastric and duodenal tracts, by means of the ingestion of $^{13}C$-labeled urea and breath detection of an increased level of $^{13}CO_2$. It is also feasible to use $^{15}N$-labeled urea, and to detect nitrogen-15 ammonia $^{15}NH_3$ in the breath, but this test format is not currently in use. Gastric and duodenal ulcers, non-ulcer dyspepsia and gastritis have been shown to be related to the presence of *Helicobacter pylori* infections.

(b) The detection of fat malabsorption, such as is present in steatorrhea and Crohn's disease, by means of the ingestion of $^{13}C$-labeled triolein or tripalmitin, and breath detection of an increased level of $^{13}CO_2$.

(c) Liver function evaluation (by monitoring the P450 enzyme activity), liver disease severity and detoxification activity by means of the ingestion of $^{13}C$-labeled aminopyrin, methacitin or caffeine citrate (depending on the specific function being tested) and breath detection of an increased level of $^{13}CO_2$.

(d) The measurement of hepatic mitochondrial activity by means of the ingestion of $^{13}C$-labeled octanoic acid, and breath detection of an increased level of $^{13}CO_2$.

(e) A check of hepatic mitochondrial function efficiency by means of the ingestion of $^{13}C$-labeled ketoisocaproic acid, and breath detection of an increased level of $^{13}CO_2$.

(f) The quantification of functional liver mass by means of the ingestion of $^{13}C$-labeled galactose, and breath detection of an increased level of $^{13}CO_2$.

(g) The testing of gastric emptying function by means of the ingestion of $^{13}C$-labeled octanoic acid for the emptying rate of solids, or $^{13}C$-labeled sodium acetate for the emptying rate of liquids, and breath detection of an increased level of $^{13}CO_2$ (h) The determination of exocrine pancreatic insufficiency by means of the ingestion of a $^{13}C$-labeled mixed triglyceride sample such as octanoil-1,3-distearin for checking the lipase function, or a $^{13}C$-labeled sample of corn starch for checking the amylase function, and breath detection of an increased level of $^{13}CO_2$. The mixed triglyceride test is one of the tests used for detecting cystic fibrosis. For the evaluation of the digestion and absorption of medium-chain fatty acid triglycerides, $^{13}C$-labeled trioctanoin is used in preference to the mixed triglyceride.

(i) The detection of bacterial overgrowth in the small intestine by means of the ingestion of $^{13}C$-labeled glycolic acid or xylose, and breath detection of an increased level of $^{13}CO_2$.

(j) The testing of lactose or glucose intolerance, by means of the ingestion of $^{13}C$-labeled lactose or glucose, and measurement of the speed of appearance of an increased level of $^{13}CO_2$ in the breath.

Previously available tests for these illnesses generally involve drastically more invasive procedures, and are therefore much less patient compliant than the simple breath tests described above. Such procedures include gastro-endoscopy, with or without the removal of a tissue biopsy, biopsies of organs suspected of malfunction, blood tests to detect antibodies to suspected bacteria, blood biochemistry tests following ingestion of suitable compounds, and radiological tests, whether by gamma imaging of the organ function following ingestion or injection of a suitable gamma emitter, or by direct X-ray imaging or CT scanning. Furthermore, there are other disadvantages to the previously used tests, such as the fact that they rarely give real time information about the organ function or status being observed. In some cases, such as in the case of blood tests for antibodies of bacterial infections, they give historic results which may have no therapeutic relevance currently, since antibodies to a particular bacterium can remain in the body for up to 2 years from the date that the infection has been eradicated.

The above mentioned breath tests are completely non-invasive, and are executed in comparative real time, so that they have a great advantage over previously available tests, and their use is gaining popularity in the medical community, as evidenced by the fact that suitable isotopically labeled substances are currently available commercially from a number of sources.

However, in spite of the advantages of isotopically labeled breath tests, current instrumentation and procedures for performing it still have a number of serious drawbacks, which continue to limit its usefulness. The major disadvantage, which becomes apparent when a review of prior art breath test performance techniques and instrumentation is performed, is that none of the currently used techniques are sufficiently rapid to permit immediate measurement of the requested parameter, allowing a diagnosis for the patient in a single short visit to the physicians office.

One of the early breath tests to be proposed is that for detecting the presence of the *Helicobacter pylori* bacterium in the upper gastro-intestinal tract, by means of the oral administration of isotopically labeled urea, and the detection of the presence of isotopically labeled carbon dioxide or ammonia in the patient's breath resulting from the hydrolysis of the urea by the urease which always accompanies *H. pylori* infections. This method is described by Marshall in U.S. Pat. No. 4,830,010. In this implementation of the test, the breath of the subject is collected, preferably from 10 to 120 minutes after administration of the substance, in a balloon inflated by the subject, and from there is transferred to a storage and transport container, such as a Vacutainer® sold by Becton-Dickenson Inc.

According to a method proposed by Marshall, the sample is then analysed by mass spectrometry or by infra-red or nuclear magnetic resonance spectroscopy, for the presence of isotopically labelled $CO_2$ resulting from the hydrolysis of the urea. If the radioactive carbon-14 is used to label the urea, then the breath sample is analysed by bubbling it through a scintillation solution, which is transferred to a scintillation counter to determine the presence of beta radiation in the exhaled breath specimen. Because of the cost and complexity of the analysis instrumentation, in none of the preferred methods described by Marshall is it suggested that the analysis of the breath may be performed on site at the point where the sample is taken from the patient. The subject must thus wait at least ten minutes to give the sample, and must then wait for the laboratory to return the results. Clearly this method cannot be used to provide the results of the test within the context of a single visit to the office of the physician.

In a recent article entitled "Minimum Analysis Requirements for the Detection of *Helicobacter pylori* Infection by the $^{13}$C-Urea Breath Test" by P. D. Klieg and D. Y. Graham, published in Am. J. Gastroenterol., Vol. 88, pp. 1865–1869, 1993, a statistical study of the reliability and minimum criteria for conducting this test is presented. The breath analyses were again performed by gas isotope ratio mass spectrometry at a remote site. Amongst their findings are that breath sampling at 30 minutes after urea ingestion is likely to lead to significantly less false-positive and false-negative results, than sampling after 20 minutes, and that sampling after 30 minutes is therefore their proposed protocol time. They also conclude that "In the current environments of clinical research and patient care, the costs and turnaround times of $CO_2$ isotopic abundance measurements continue as the major barriers to commercial propagation of the $^{13}$C-urea breath test."

In another described prior art method of executing the urea breath test, Koletzko and co-workers describe the analysis of the exhaled breath by means of an isotope-selective non-dispersive infrared spectrometer [Koletzko et al., Lancet, 345:961-2, 1995]. Even using such a sophisticated instrument, the subjects are still required to wait 15 and 30 minutes for successive breath samples to be taken. Such a long delay to obtain breath samples, as well as the long wait between samples, is inconvenient and potentially reduces patient compliance.

Furthermore, as in the previously mentioned prior art, the sample or samples are collected from the patient and then sent to a laboratory for analysis, causing a delay in the determination of the results and forcing the subject to return to the office of the physician to obtain the results. If the test does not yield meaningful results, the entire process must be repeated again. The requirement for multiple office visits potentially further reduces patient compliance. The potential reduction in patient compliance can have serious consequences, since *Helicobacter pylori* is implicated by the World Health Organisation as a possible cause of stomach cancer, in addition to its role in gastric and duodenal ulcers.

The most rapid breath test currently proposed, the "Pytest" from Tri-Med Specialties, Charlottesville, N.C., USA, takes about 10–15 minutes to perform but uses radioactive carbon-14 isotopically-labeled urea [D. A. Peura, et al., Am. J. Gastro., 91:233–238, 1996]. The presence of $^{14}CO_2$ in the subject's exhaled breath is detected by direct beta counting. This test thus has all the disadvantages of the use of radioactive materials. Not only is the ingestion of radioactive materials potentially hazardous, but it also restricts the test to large testing centers which can handle such materials. Thus, the test cannot be performed in the office of the average physician, so that multiple office visits are again required.

Another recent prior art method which discusses implementations of the $^{13}$C-urea breath test, is shown in PCT Application No. WO97/14029, entitled "Method for Spectrometrically Measuring Isotopic Gas and Apparatus thereof", applied for by the Otsuka Pharmaceutical Company of Tokyo, Japan. In this application too, the exhaled breath sample is transferred in sample bags from the patient to the spectrometer, which, because of its cost, complexity and size, has perforce to be installed in a central sample collection laboratory, and not in the doctor's office or near the patient's bed. The inventors in fact state that "The measurement of such breath samples is typically performed in a professional manner in a measurement organisation, which manipulates a large amount of samples in a short time." This prior art proposes the use of one breath sample before the administration of the urea, and another after a lapse of 10 to 15 minutes.

Other prior art which describe sensitive analyzer systems for measuring the isotopic ratios of $^{13}CO_2$ to $^{12}CO_2$ in a gaseous sample, such as is required in an exhaled breath analyzer for performing the above mentioned breath tests, includes U.S. Pat. No. 5,077,469, granted to W. Fabinski and G. Bernhardt, which describes a double reference path non-dispersive infra-red gas analyzer. A further development of such an instrument described in European Patent Application No. EP 0 584 897 A1 can be used to compare the two isotopic $CO_2$ concentrations in the exhaled breath by means of infra-red absorption measurements on two IR-cells filled with gas from the same breath sample.

In U.S. Pat. Nos. 4,684,805 and RE 33493, granted to P. S. Lee, R. F. Majkowski and D. L. Partin, an infra-red absorbtion spectrometer is described for discriminating between the two isotopic $CO_2$ molecules for the breath tests. Their spectrometer design uses lead salt laser diodes as the source of radiation. Such laser diodes have emission lines in the 4 $\mu$m to 5 $\mu$m wavelength region of the infra-red spectrum, where the strongest $CO_2$ absorption lines are located. As a consequence, despite the lack of temperature stability of such laser diodes, and the fact that they must be operated at liquid nitrogen temperatures, their use enables the spectrometer to achieve the high selectivity and sensitivity required for breath test analysis.

U.S. Pat. No. 5,317,156, granted to D. E. Cooper, C. B. Carlisle and H. Riris, describes an FMS (Frequency Modulation Spectroscopy) laser absorption spectrometer for distinguishing between the weak $^{12}CO_2$ and $^{13}CO_2$ absorption lines in the 1.6 $\mu$m infra-red region, where highly stable laser diodes are available. Even though the $CO_2$ lines are very weak in this region, the stability of the GaAs laser diodes used as the source in this range, and the sophisticated TTFMS (two-tone Frequency Modulation Spectroscopy) technique used enables the inventors to provide sufficient differentiation between the two isotopes of $CO_2$ that the spectrometer can be used in breath test analysis.

In U.S. Pat. No. 5,394,236, granted to D. E. Murnick, an apparatus for isotopic analysis of $CO_2$ is described by means of laser excited spectroscopy, utilising the optogalvanic effect to differentiate between the light of different wavelengths.

Because of the need to provide high sensitivity and good mass discrimination, all of the above described analysis systems are complex in nature. They are therefore, costly to manufacture and generally of large dimensions, making them suitable for commercial exploitation only for large and high sample volume installations.

A number of commercial companies offer complete systems for performing breath tests for the detection and study of the various gastro-enterologic conditions mentioned previously, using the isotopically labeled substances commercially available.

The Alimenterics Company of Morris Plains, N.J., markets the Pylori-Chek $^{13}$C-Urea breath test kit for use with its LARA™ System, for detecting the presence of *H. Pylori* in the gastro-intestinal tract. The company is developing kits for the clinical use of the other breath tests mentioned above. Breath is collected in a uniquely designed breath collection device, that also serves to transport the sample to the LARA™ System. This system, which stands for Laser Assisted Ratio Analyzer, is a sophisticated infra-red spectrometer designed to provide the sensitivity required to detect tiny percentage changes in the level of $^{13}CO_2$ in the patient's exhaled breath. Because of the complexity of the LARA™ System, it is a large piece of equipment, weighing over 300 kg, and very costly. Consequently, this system too is only feasible for very large institutions and central laboratories, where the large number of tests performed can justify the cost.

Meretek Diagnostics Incorporated of Nashville, Tenn., has also developed such a $^{13}$C-Urea breath test diagnostic system, and use an isotope ratio mass spectrometer called the ABCA (Automated Breath $^{13}$C Analyzer) manufactured by Europa Scientific Limited, of Crewe, Cheshire, U.K. for analyzing the breath samples. In this system too, the analyzer unit is large, costly and sophisticated, and therefore is usually located remote from the collection point.

Wagner Analysen Technik GmbH of Worpswede, Germany, offers an infra-red non-dispersive spectrophotometer-based system called the IRIS®—Infra Red ISotope Analyser, which is based on the above-mentioned European Patent Application No. EP 0 584 897 A1. Though the main useage mode is by means of transport of the breath samples from the collection point to the analyzer in sample bags, this system, according to the manufacturer's sales literature, also has a sample port whereby connection can be made directly to a breathing mask, an incubator, or a breathing machine. No details of such a connection tube accessory are however given in the technical manual accompanying the analyzer, nor does the manufacturer provide any programs with the system's operational software to enable such an accessory to be used for performing on-line analyses. This analyzer has dimensions of 510×500×280 mm and weighs 12 kg., and in addition, a PC is required for control. Though smaller and less costly than those mentioned above, it is still too large and heavy to be described as a truly portable device. Furthermore, its reported cost of several tens of thousands of U.S. Dollars, though considerably less than that of the two above-mentioned commercial systems, still makes it unsuitable for point-of-care or physician's office use.

In the preferred procedures described in all of the above mentioned prior art, the patient must wait typically 20–30 minutes before the active sample is collected, mainly because only one sample is taken beyond a background sample. This time is necessary to allow the level of isotopically labeled exhaled gas to reach a relatively high value, close to its end value, to enable the analyzer to measure the gas with a sufficient confidence level. However, such a single point determination potentially decreases the accuracy of the test, as well as increasing the risk of ambiguous results.

To the best of our knowledge, no breath test analyzer system has been described in the prior art which is sufficiently small, fast in producing reliable results, low in production cost, portable and sensitive, to enable it to be used as for executing tests in real time in the physician's office or at another point of care.

SUMMARY OF THE INVENTION

The present invention seeks to provide an improved breath test analyzer which overcomes disadvantages and drawbacks of existing analyzers, which provides accurate results on-site in times of the order of minutes, and which is capable of implementation as a low cost, low volume and weight, portable instrument. The breath analyzer of the present invention is sufficiently sensitive to enable it to continuously collect and analyze multiple samples of the patient's breath from the beginning of the test, and process the outputs in real time, such that a definitive result is obtained within a short period of time, such as of the order of a few minutes.

Such a breath test analyzer is suitable for the detection of various disorders or infections of the gastro-intestinal tract, or metabolic or organ malfunctions, and since it can provide results in real time without the need to send the sample away to a special testing center or central laboratory, can be used to provide diagnostic information to the patient in the context of a single visit to a physician's office, or at any other point of care in a health care facility.

In accordance with a preferred embodiment of the present invention, there is provided a breath test analyzer, including a very sensitive gas analyzer, capable of measuring the ratio of two chemically identical gases but with different molecular weights, resulting from the replacement of at least one of the atoms of the gas with the same atom but of different isotopic value. Since the isotopically labeled gas to be measured in the patient's breath may be present only in very tiny quantities, and since, in general, it has an infra-red absorption spectrum very close to that of the non-isotopically labeled gas, the gas analyzer must be capable of very high selectivity and sensitivity, to detect and measure down to the order of a few parts per million of the host gas.

The breath test analyzer is also sufficiently small that it can easily be accomodated in the office of a physician, such as a gastro-enterologist, and its cost is also sufficiently low that its use in such an environment can be economically justified.

There are a number of different operational modes for each type of test for such a breath analyzer, the common denometer being that the analysis is performed in real time whilst the patient is continuing to provide breath for subsequent analyses. In the most common mode of operation, the breath test analyzer senses a patient's exhaled breath before ingestion of an isotopically labeled substance, analyzes the patient's exhaled breath for the percentage of the isotopically labeled gas in the total exhaled gas of that composition in order to obtain a baseline reading, performs at least one similar analysis after ingestion of an isotopically labeled substance, and provides an indication of a medical condition within a time period following the last sensing which is less than the difference in time between the first sensing of the patient's exhaled breath and the second sensing. This delineates it from previous breath analyzers, which, because of the generally remote location of the analyzer from the point at which the samples are given, cannot provide this indication within such a time limit.

In an alternative mode of operation, the analyses are made successively at times after ingestion of an isotopically labeled substance, and before the end of production of the isotopically labeled by-products of the substance, and the analyzer performs comparisons of the change from sample to sample of the percentage of the isotopically labeled gas in the total exhaled gas of that composition, and thereby provides an indication of a medical condition as soon as the detected change in gas composition percentage permits it, and before the end of production of the isotopically labeled by-products of the substance.

There are also two modes of analyzing the breath samples. The analyser can either perform its analysis on individual exhaled breaths, or, as stated above, it can perform its analysis on multiple samples of the patient's breath, continuously collected from the patient. The method of collection and subsequent analysis of multiple samples of the patient's breath has been described in co-pending Israel Patent Application No. 121793, which is hereby incorporated by reference. That application described an analyzer wherein the patient's breaths are exhaled into a resevoir for collection, in this application called a breath collection chamber, and transferred from there by one of various methods to the sample measurement chamber. One of the advantages of the method described therein, is that the analyzer draws an averaged sample of breath for measurement, instead of individual breaths, thereby increasing accuracy. Another advantage is that it is possible, by suitable valving means, to collect only the plateau parts of multiple breaths for analysis.

In accordance with a further preferred embodiment of the present invention, there is provided a breath test analyzer, which analyzes a first exhaled breath of a patient and a second exhaled breath of the patient for isotope labeled products generated in the patient's body after ingestion by the patient of an isotope labeled substance, by performing a first analyzing of the patient's first breath and a second analyzing of the patient's second breath, at least the second breath being exhaled following patient's ingesting the substance, the analyzer providing an indication of a medical condition within a time period following the exhalation of the second breath which is less than the difference in time between the exhalation of the first breath and the exhalation of the second breath.

There is further provided in accordance with yet another preferred embodiment of the present invention, a breath test analyzer as described above and including a breath analysis chamber, a breath inlet conduit for conveying exhaled gas from a patient to the breath analysis chamber; and a gas analyzer operative to analyze gas in the breath analysis chamber and to conduct the first analyzing of gas exhaled by the patient's first breath and the second analyzing of the patient's second breath, at least the second breath being exhaled following ingestion by the patient of an isotope labeled substance.

Furthermore, for those preferred embodiments which analyze samples collected from exhaled breaths of a patient, instead of individual breaths, it is understood that the analyzer also incorporates a breath collection chamber, which may be a separate chamber, or part of the breath inlet conduit, or part of the breath analysis chamber. In the latter case, the analysis of the gas sample effectively takes place in the breath collection chamber.

In accordance with another preferred embodiment of the present invention, there is provided a breath test analyzer as described above, and wherein the patient's first breath is exhaled prior to ingestion of an isotopically labeled substance, and the patient's second breath is exhaled following ingestation of the isotopically labeled substance.

In accordance with yet another preferred embodiment of the present invention, there is provided a breath test analyzer as described above, and wherein both of the patient's first and second breaths are exhaled following patient's ingestation of the isotopically labeled substance.

There is further provided in accordance with another preferred embodiment of the present invention, a breath test analyzer which analyzes a patient's breath for isotope labeled products generated in the patient's body after ingestion by the patient of an isotope labeled substance, the analyzer providing an indication of a medical condition existent in the patient by analyzing at least two successive samples of the patient's breath, wherein the at least two successive samples of the patient's breath include at least one later sample exhaled following analysis of at least one earlier sample.

There is still further provided in accordance with another preferred embodiment of the present invention, a breath test analyzer as described above and including a breath analysis chamber, a breath inlet conduit for conveying exhaled gas from a patient to the breath analysis chamber, and a gas analyzer operative to analyze gas in the breath analysis chamber and to conduct analyses of the at least two successive samples of the patient's breath, wherein the at least two successive samples of the patient's breath include at least one later sample exhaled following analysis of at least one earlier sample.

In accordance with still another preferred embodiment of the present invention, there is provided a breath test analyzer which analyzes a patient's exhaled breath before and after a product of an isotope labeled substance ingested by the patient could be detected in the patient's breath, a first analyzing of the patient's exhaled breath taking place prior to the product being detectable in the patient's breath and a second analyzing of the patient's exhaled breath taking place once the product could be detectable in the patient's breath, the analyzer providing an indication of a medical condition within a time period following the exhalation of the second breath which is less than the difference in time between the exhalation of the first breath and the exhalation of the second breath.

There is further provided in accordance with other preferred embodiments of the present invention, a breath test analyzer which analyzes a first exhaled breath of a patient and a second exhaled breath of the patient for the products of an isotope labeled substance ingested by the patient while the patient is coupled to the device, or analyzes the above mentioned exhaled breath and provides an indication of a medical condition while the patient is coupled to the device, or is breathing into the device. The patient whose breath is being analyzed can be coupled to the device continuously from the analyzing of the first exhaled breath to the analyzing of the second exhaled breath.

There is still further provided in accordance with another preferred embodiment of the present invention, a breath test analyzer as described above and including a breath analysis chamber, a breath inlet conduit for conveying exhaled gas from a patient to the breath analysis chamber, and a gas analyzer operative to analyze gas in the breath analysis chamber while the patient is coupled to the device.

There is even further provided in accordance with still another preferred embodiment of the present invention, a breath test analyzer as described above and including a breath analysis chamber, a breath inlet conduit for conveying exhaled gas from a patient to the breath analysis chamber, and a gas analyzer operative to analyze gas in the breath analysis chamber and to provide an indication of a medical condition while the patient is coupled to the device.

There is also provided in accordance with another preferred embodiment of the present invention, a breath test analyzer as described above and including a breath analysis chamber, a breath inlet conduit for conveying exhaled gas from a patient to the breath analysis chamber; and a gas analyzer operative to analyze gas in the breath analysis chamber and to provide an indication of a medical condition while the patient is breathing into the device.

In accordance with still another preferred embodiment of the present invention, there is provided a breath test analyzer as described above and wherein the patient is coupled to a disposable breath input device.

In accordance with yet another preferred embodiment of the present invention, there is provided a medical sample analyzer which analyzes samples taken from a patient, and wherein either the taking or the analyzing of the samples is terminated automatically at a point in time determined by the results of the analyzing of the samples.

In accordance with even another preferred embodiment of the present invention, there is further provided a breath test analyzer which analyzes samples of a patient's breath for isotope labeled products generated in the patient's body after ingestion by the patient of an isotope labeled substance, and wherein either the taking or the analyzing of the samples is terminated automatically at a point in time determined by the results of the analyzing of samples.

There is also provided in accordance with another preferred embodiment of the present invention, a medical sample analyzer as described above, which analyzes samples taken from a patient and including a sample input port for receiving samples taken from the patient and an analyzing apparatus for analyzing the samples, and wherein the analyzing is terminated automatically at a point in time determined by the results of the analyzing of the samples.

There is further provided in accordance with another preferred embodiment of the present invention, a breath test analyzer as described above and including a breath analysis chamber, a breath inlet conduit for conveying exhaled gas from a patient to the breath analysis chamber; and a gas analyzer operative to analyze gas in the breath analysis chamber and wherein the analyzing of samples from the patient is terminated automatically at a point in time determined by the results of the analyzing of the samples.

In accordance with another preferred embodiment of the present invention, there is further provided a breath test analyzer as described above, and wherein the gas analyzer includes a gas discharge tube gas analyzer, or an infra-red source which emits a discontinuous spectrum.

In accordance with yet another preferred embodiment of the present invention, there is provided a breath test analyzer as described above, and wherein the results of the analyzing of successive samples are fitted to a curve, and an indication of a medical condition in a patient is determined by inspecting the derivative of the curve.

In accordance with even another preferred embodiment of the present invention, there is further provided a method of breath testing which analyzes a first exhaled breath of a patient and a second exhaled breath of the patient for isotope labeled products generated in the patient's body after ingestion by the patient of an isotope labeled substance, and comprising the steps of performing a first analyzing of the patient's first breath, subsequently performing a second analyzing of the patient's second breath, at least the second breath being exhaled following the patient's ingesting the substance, and providing an indication of a medical condition within a time period following exhalation of the second breath which is less than the difference in time between exhalation of the first breath and exhalation of the second breath.

There is further provided in accordance with another preferred embodiment of the present invention, a method of breath testing which analyzes a patient's exhaled breath for the product of an isotope labeled substance ingested by the patient, and comprising the steps of performing a first analyzing of the patient's exhaled breath prior to the product being detectable in the patient's breath, performing a second analyzing of the patient's exhaled breath once the product is detectable in the patient's breath, and providing an indication of a medical condition within a time period following the exhalation of the second breath which is less than the difference in time between the exhalation of the first breath and the exhalation of the second breath.

Furthermore, whereas all of the above mentioned preferred embodiments have been described for breath analyzers which analyze a first exhaled breath of a patient and a second exhaled breath of the patient, it is understood that the operation of these preferred embodiments are equally valid for breath analyzer which analyze a first sample collected from at least a first exhaled breath of a patient, and a second sample collected from at least a second exhaled breath of a patient.

BRIEF DESCRIPTION OF THE DRAWINGS

The present invention will be understood and appreciated more fully from the following detailed description, taken in conjunction with the drawings, in which:

In FIG. 3A, the patient is shown at time $t_0$ providing the reference breath before taking the isotopically labeled substance suitable for the specific test to be performed.

FIG. 3B shows the patient at time $t_1$ ingesting the isotopically labeled substance, shown in this instance in a glass of liquid.

FIG. 3C is a view of the patient at time $t_2$ providing continuous breath samples for the analyzer to collect through the nasal cannula or breathing tube. The analyzer itself measures the level of the isotopically labeled gas sample at regular intervals, and under the control of the PC, calculates the ratio of the isotopically labeled gas level to that of the naturally occuring gas of the same species for every breath sample, and subtracts the ratio from the baseline reference breath level. These ratios, known as the delta-over-baseline values, are fitted to a curve of ratio as a function of time, from which the results of the test can be deduced.

FIG. 3D shows the situation at time $t_3$ when the test has been completed and analysis terminated, either because the desired percentage level of the isotopically labeled gas has been reached, or because a time limit has been reached without a definitive delta-over-baseline percentage of gas having been reached. The PC is ready to show the results of the analysis prior to printout. Since the test is complete, the patient has removed the sampling device.

In FIG. 4A, the patient is shown at time $t_0$ ingesting the isotopically labeled substance, in this example in a glass of liquid.

In FIG. 4B, the patient is shown at time $t_1$ providing continuous breath samples for the analyzer to collect through the nasal cannula or breathing tube. The analyzer itself is measuring the level of the isotopically labeled gas sample at regular intervals, and under the control of the PC, is continuously calculating the ratio of the isotopically labeled gas level as compared to that of the previous measurement, in order to obtain a comparative reading of the change in the percentage level of the isotopically labeled gas from reading to reading as the breath test proceeds.

FIG. 4C shows the situation at time $t_2$ when the test has been completed and analysis terminated, either because the desired percentage increase in the level of the isotopically labeled gas has been reached, or because a time limit has been reached without a definitive percentage change having been detected. The display screen of the PC shows the results of the analysis prior to printout. Since the test is complete, the patient has removed the sampling device.

DETAILED DESCRIPTIONS OF PREFERRED EMBODIMENTS

Figure 1:
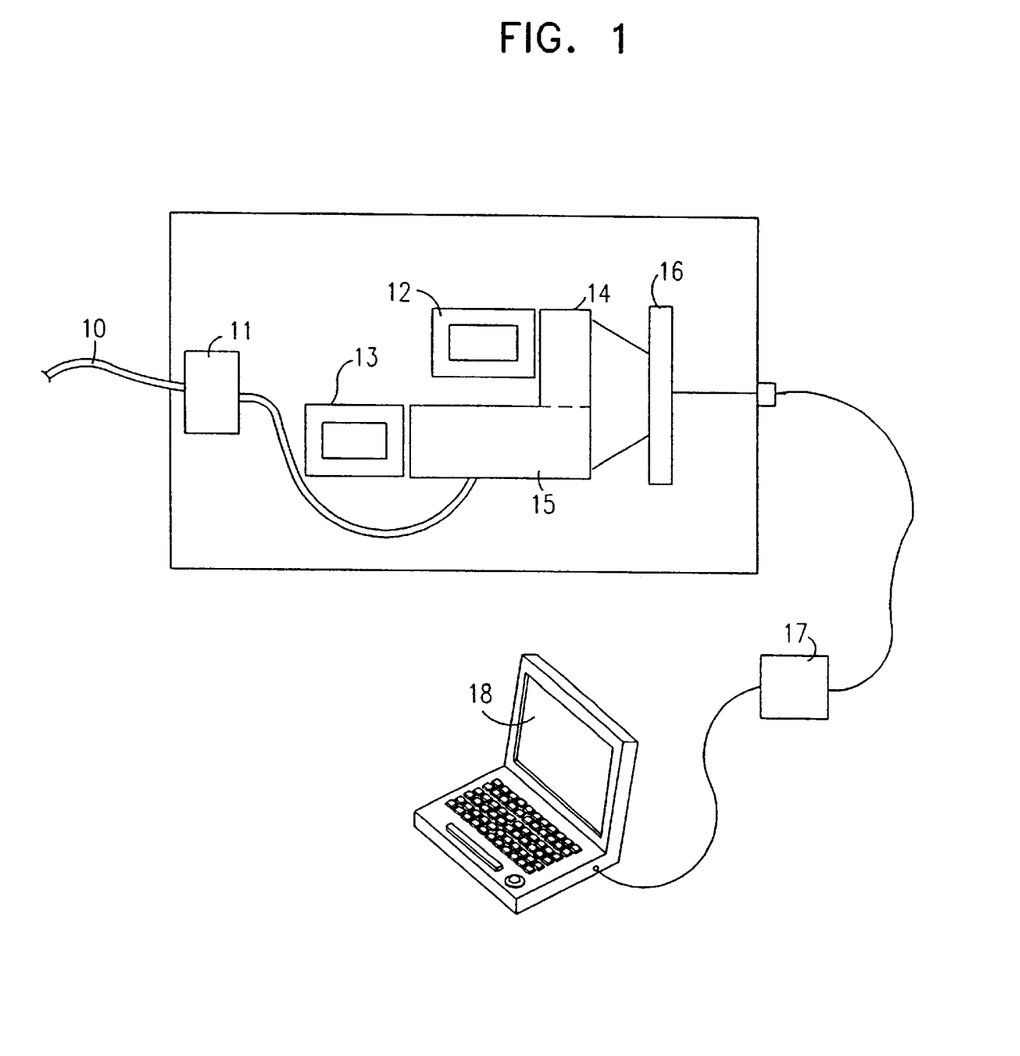
FIG. 1 is a schematic view of a breath analyzer constructed and operative in accordance with a preferred embodiment of the present invention, showing its main component parts including the breath inlet conduit and the breath analysis chamber.

Reference is now made to FIG. 1, which is a schematic view of a compact high sensitivity breath analyzer constructed and operative in accordance with a preferred embodiment of the present invention. The breath analysis is performed by a sensitive non-dispersive infra-red spectrophotometer, capable of discriminating between the isotopically labeled $CO_2$ and the natural $CO_2$ in the breath sample being analyzed.

The patient is connected to the breath analyzer by means of the inlet tube 10, which can be either a nasal cannula or a breathing tube. Such a cannula includes a section of tubing, usually plastic, with two prongs. Each prong is inserted into a nostril and the cannula is then connected to the measuring instrument. As the patient exhales through the nose, a sample of the exhaled air flows through the cannula to the analyzer. A preferred type of breathing tube is constructed of a hollow tube held in the patient's mouth, through which he blows a number of breathes. In the center of the tube is located a small tube whose opening is positioned such that it samples the breath flowing through the main tube, and conveys it through a small flexible plastic inlet tube to the breath analyzer.

The patient's breath is inputted to the breath inlet conduit 11, which could also incorporate a breath collection chamber for acumulating a number of breaths, from where the breath sample is conveyed to the breath analysis chambers 14, 15 of a non-dispersive infra-red spectrophotometer. The breath analysis chamber could also be part of the breath collection chamber, such that the analysis is performed in the breath collection chamber. The spectrophotometer preferably uses gas discharge lamp sources 12, 13, such as those provided by Spegas Industries of Jerusalem, Israel. Such lamps enclose an enriched and nearly pure filling of $^{12}CO_2$ or $^{13}CO_2$ respectively. By excitation of an RF field, the gas discharge generates an emission which is typical of the $CO_2$ enclosed within the lamp. The average width of the emission lines from these lamps is only 0.006 $cm^{-1}$, such that there is little cross-sensitivity. It is possible to detect a change in isotopic gas concentration of the order of a few parts per million.

In order to obtain the ratio of $^{13}CO_2/^{12}CO_2$ of a breath sample, the absorption of the sample is measured with a $^{12}CO_2$ lamp and a $^{13}CO_2$ lamp as light source. Such lamps have been used in a spectro-photometer described in U.S.

Pat. No. 5,063,275 incorporated herein by reference. The output signals are measured on an infra-red detector 16. The signals from this detector are processed electronically by the analyzer's electronics unit 17, and the resulting ratio output signal passed to the PC 18 for analysis by the system software according to the requirements of the measurement program.

Figure 2A:
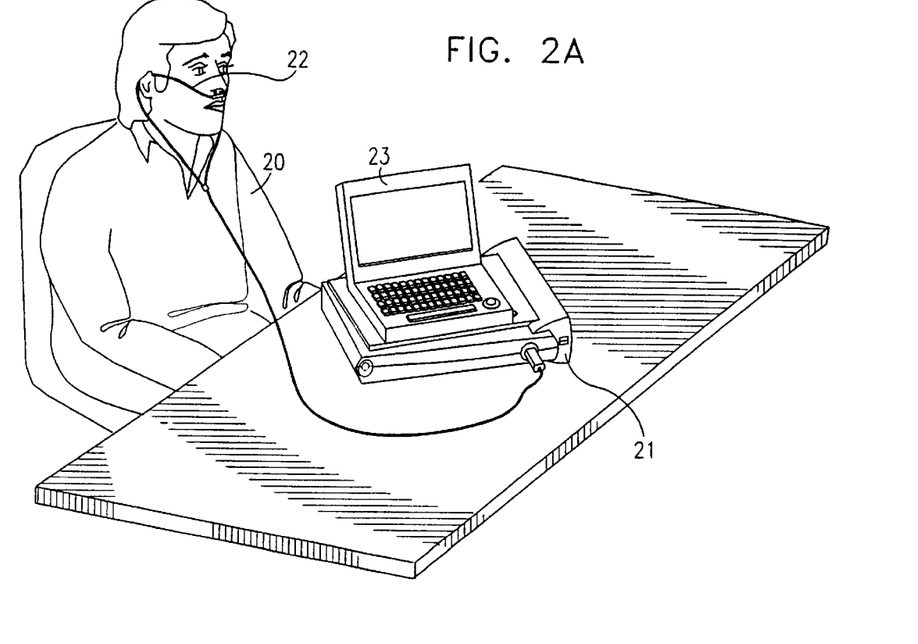
FIG. 2A is a schematic view of a patient connected to the breath test analyzer by means of a nasal cannula, and shows the compact size of the analyzer, together with its associated laptop PC used for controlling the analyzer.
Figure 2B:
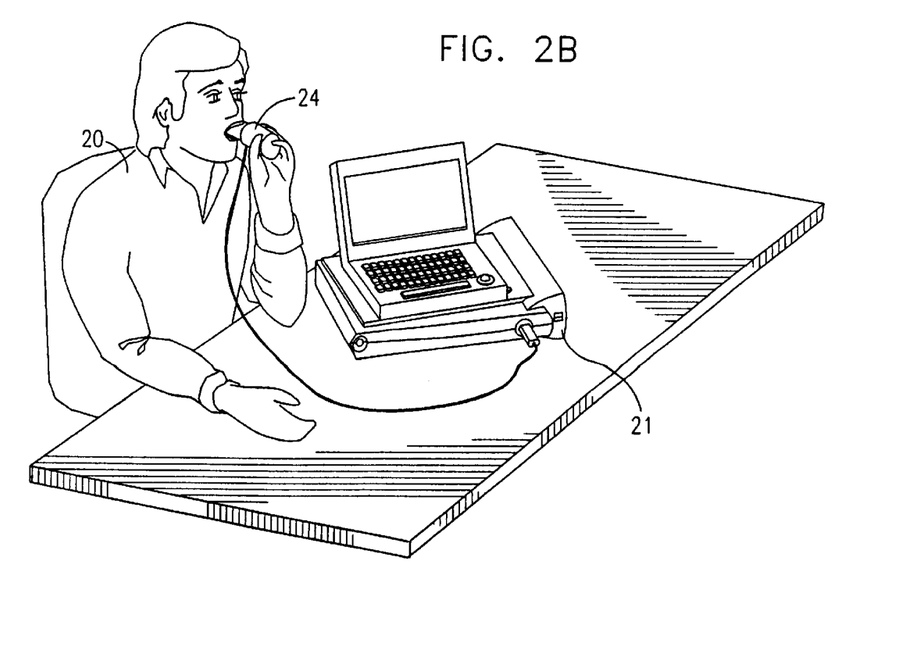
FIG. 2B is similar to FIG. 2A, except that the patient is connected to the analyzer by means of a blowing tube which he puts into his mouth when a sample breath is required.

FIG. 2A is a schematic view of a patient 20 connected by means of a nasal cannula 22, to a breath test analyzer 21 constructed and operative according to a preferred embodiment of the present invention. A laptop PC 23 is used for controlling the analyzer. The compact size of the analyzer is apparent, when compared with the size of the laptop PC which stands on it. FIG. 2B is similar to FIG. 2A, except that the patient 20 is connected to the breath analyzer 21 by means of a blowing tube 24 which he puts into his mouth whenever sample breaths are required.

FIGS. 3A to 3D show schematically the various steps of a complete breath test cycle in the most common mode of operation. The test cycle is shown being performed using a nasal cannula 30 for the breath sampling, but the same procedure can be performed with the samples collected by means of a mouth tube. In the most common mode of operation, the breath test analyzer senses a patient's breath before ingestion of an isotopically labeled substance, analyzes the patient's exhaled breath for the percentage of the isotopically labeled gas in the total exhaled gas of that composition in order to obtain a baseline reading, performs at least one similar analysis after ingestion of an isotopically labeled substance, and provides an indication of the increased presence of the isotopically labeled by-products characteristic of a medical condition, within a time period following the last sensing which is less than the difference in time between the first sensing and the last sensing. The analyses of the patient's exhaled breath may be performed directly, or on samples of exhaled breath collected in a breath collection chamber.

Figure 3A:
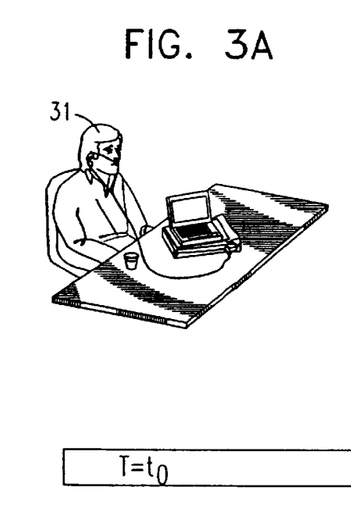
FIGS. 3A to 3D show schematically the various steps of a complete breath test cycle. The test cycle is shown being performed using a nasal cannula for the breath sampling, but the same procedure can be performed with the samples collected by means of a mouth tube.

In FIG. 3A, the patient 31 is shown at time $t_0$ providing the reference breath before taking the isotopically labeled substance suitable for the specific test to be performed. This reference breath enables the analyzer to establish a baseline level for the percentage of the isotopically labeled gas in the breath of the patient without the addition of any products of the isotopically labeled substance ingested.

Figure 3B:
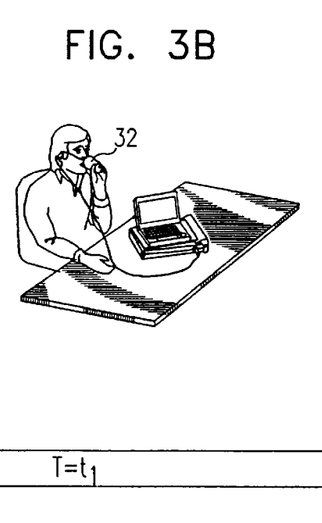

FIG. 3B shows the patient at time $t_1$ drinking the isotopically labeled substance 32, shown in this instance in a glass of liquid.

Figure 3C:
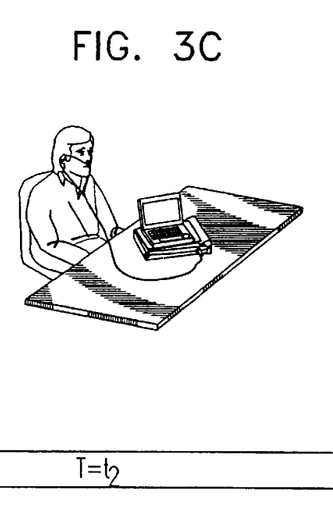

FIG. 3C is a view of the patient at time $t_2$ providing continuous breath samples for the analyzer through the nasal cannula or breathing tube. The analyzer itself measure the level of the isotopically labeled gas sample at regular intervals, and under the control of the PC, calculates the ratio of the isotopically labeled gas level to that of the naturally occuring gas of the same species for every breath sample, and subtracts the ratio from the baseline reference breath level. These ratios, known as the delta-over-baseline values, are fitted to a curve of ratio as a function of time, from which the results of the test can be deduced. Each measurement takes a number of seconds, such that the analyses of the exhaled breath are effectively performed on a quasi-continuous basis. This is one of the main features which differentiates the procedure possible using a breath analyzer constructed and operative according to the present invention from all prior art procedures.

The technique proposed here, of performing a multiplicity of analyses or measurements under control of the measurement instrument itself, is applicable to a wide range of medical instrumentation. This technique allows the construction of an analyzer or measurement instrument, wherein the termination point of the test procedure being performed is determined automatically according to the results of the analyses or tests obtained in real time. The termination of the test procedure can refer not only to the termination of the taking of samples from the patient, but also to the termination of the analysis of such samples taken from the patient at an earlier time.

In the breath analyzer according to a preferred embodiment of the present invention, the multiplicity of analyses on substantially every successive breath, or on frequent samples of collected breaths, allows the analyzer to determine the termination point of the test procedure according to the results obtained in real time. In this most common mode of operation, the measurement system obtains for every breath sample, the ratio of the level of the isotopically labeled gas to that of the naturally occurring gas being analyzed. This ratio is then compared with the baseline ratio obtained at time $t_0$ in order to determine whether a positive result is being obtained. The delta-over-baseline level chosen to define a positive result is dependent on the specific test, and its sensitivity. The method of comparison of the measurement of one breath sample with the previous one can preferably be performed by means of fitting the results to a curve by one of the standard digital curve fitting methods, and determining the derivative of the curve at every new measurement point, or by simple repetitive difference measurements.

Figure 3D:
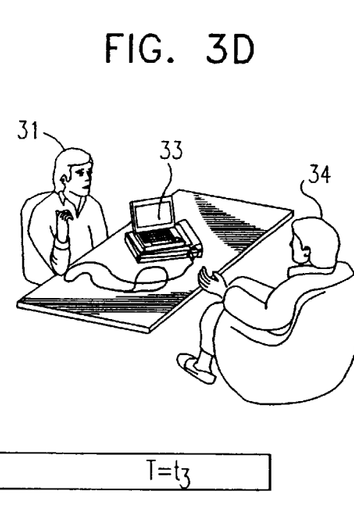

FIG. 3D shows the situation at time $t_3$ when the test has been completed and analysis terminated, either because the desired percentage increase in the level of the isotopically labeled gas has been reached, or because a time limit has been reached without a definitive delta-over-baseline percentage increase of gas having been reached. The display screen of the PC 33 shows the results of the analysis prior to printout. Since the test is complete, the patient 31 has removed the sampling device, and the patient's physician 32 is generally able to give him an immediate diagnosis, or at least the result of the test.

Figure 4A:
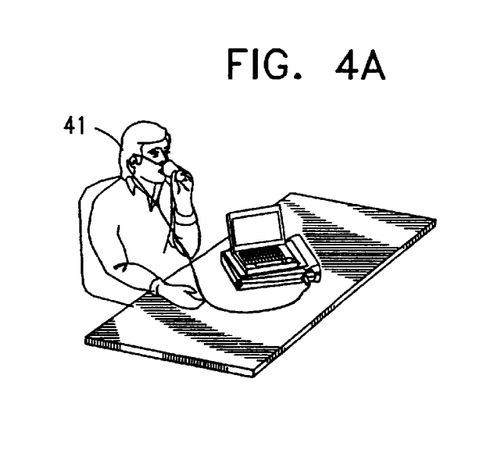
FIGS. 4A to 4C show the various stages of a complete breath test cycle according to another preferred embodiment of the present invention, where the sampling analyses are performed at times following the ingestion of the isotopically labeled substance, without the need for a baseline measurement.
Figure 4B:
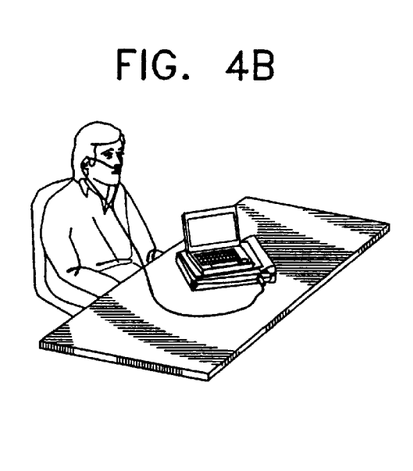
Figure 4C:
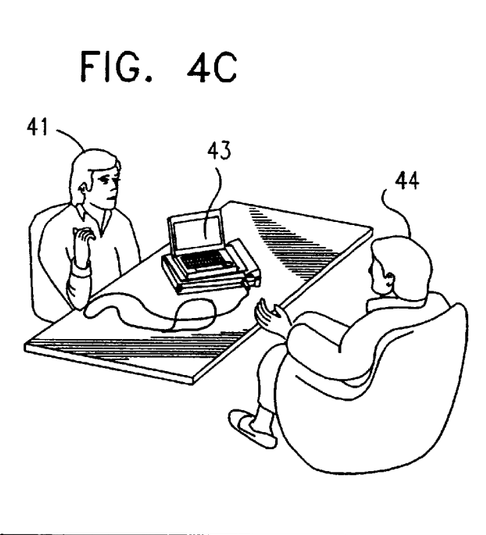

FIGS. 4A to 4C show the various stages of a complete breath test cycle according to another preferred embodiment of the present invention, where the sampling analyses are performed at times following the ingestion of the isotopically labeled substance, without the need for a baseline measurement. This mode of operation is possible only because of the on-line nature of the measurements which the present invention enables. The method of comparison of the measurement of one breath sample with the previous one, can again be preferably performed by means of fitting the results to a curve by one of the standard digital curve fitting methods, and determining the derivative of the curve at every new measurement point.

In FIG. 4A, the patient 41 is shown at time $t_0$ ingesting the isotopically labeled substance, in this example in a glass of liquid.

In FIG. 4B, the patient is shown at time $t_1$ providing continuous breath samples for the analyzer to collect through the nasal cannula or breathing tube. The analyzer itself is measuring the level of the isotopically labeled gas sample at regular intervals, and under the control of the PC, is continuously calculating the ratio of the isotopically labeled gas level as compared to that of the previous measurement, in order to obtain a comparative reading of the change in the percentage level of the isotopically labeled gas from reading to reading as the breath test proceeds. In a preferred embodiment of the present invention, the analyzer program performs digital curve fitting analysis, as described above, in order to monitor the progress of the test.

FIG. 4C shows the situation at time $t_2$ when the test has been completed and analysis terminated, either because the desired percentage increase in the level of the isotopically labeled gas has been reached, or because a time limit has been reached without a definitive percentage change having been detected. The display screen of the PC 43 shows the results of the analysis prior to printout. Since the test is complete, the patient has removed the sampling device. As previously, the patient's physician 44 is able to advise him immediately of the result of the test.

Figure 5:
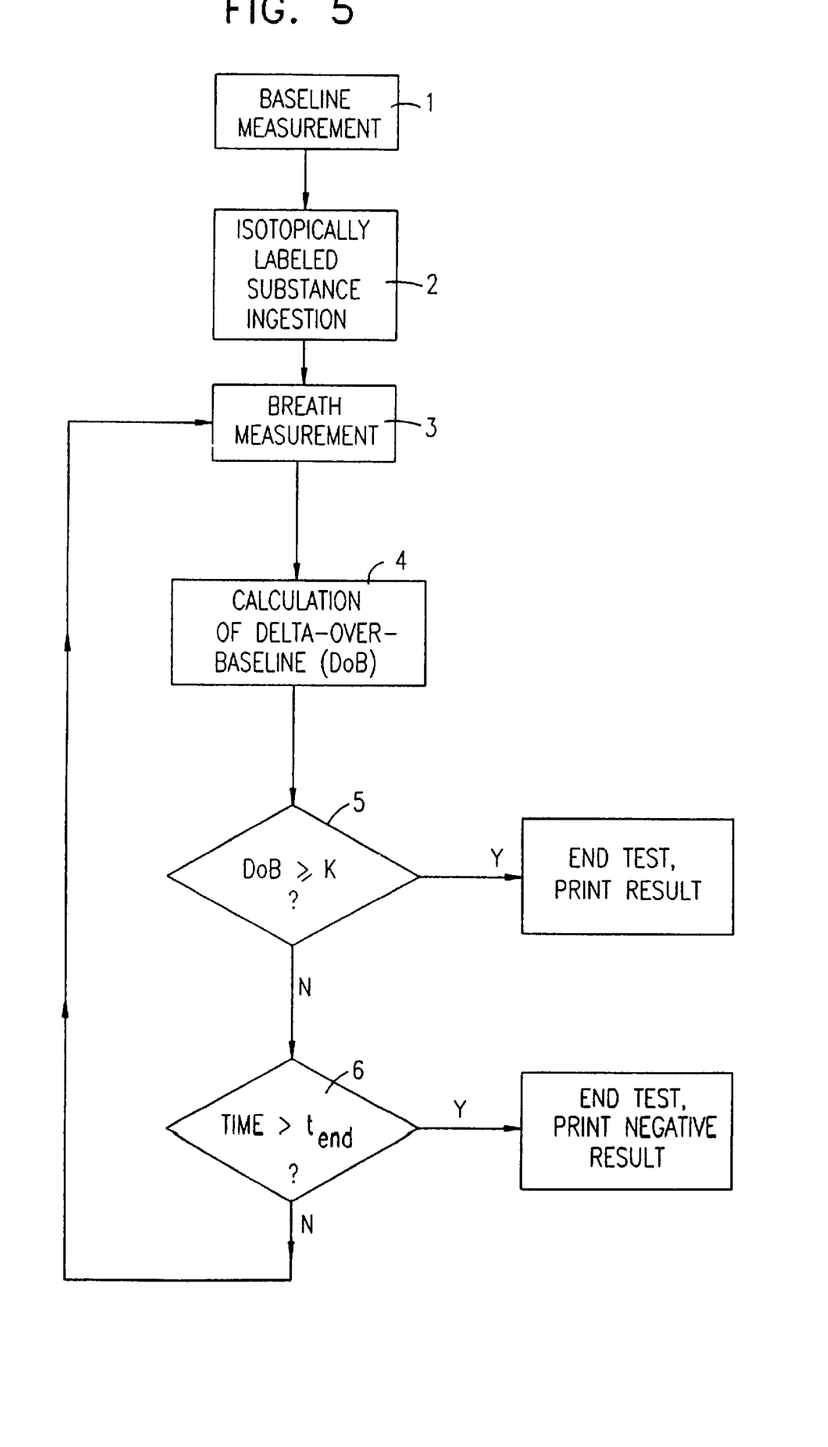
FIG. 5 is a schematic flow chart of the test procedures described in FIGS. 3A to 3D, and in FIGS. 4A to 4C.

The above mentioned operational modes of breath analyzing, and their methods of termination are functionally shown in the flow chart shown in FIG. 5, which is shown for the case when a baseline measurement is made before ingestion by the patient of the isotopically labeled substance. If no baseline measurement is made, the initial stage 1 of the flow chart is omitted, and in place of stage 4, an alternative calculation must be made, such as taking the difference between successive readings.

Figure 6:
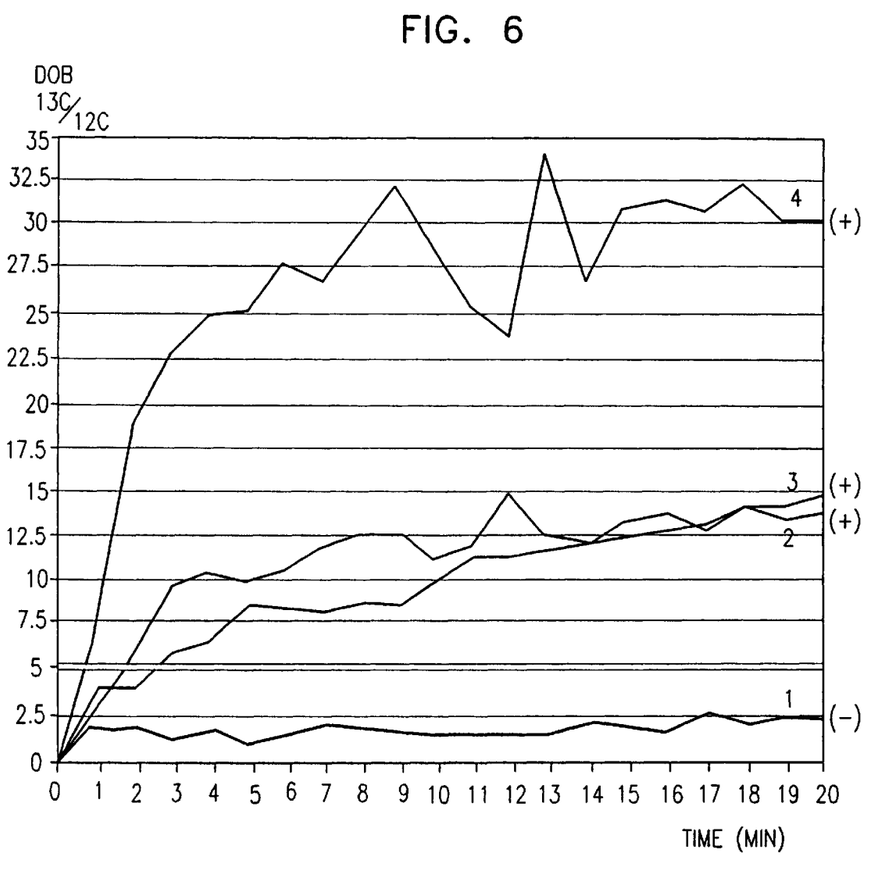
FIG. 6 shows a typical graph of the increase in ratio of the isotopically labeled gas as a function of time as the breath test proceeds, for a number of different patients.

FIG. 6 shows graphs of the increase in ratio of the isotopically labeled gas as a function of time as the breath test proceeds, for a number of different patients. The actual results shown were obtained using a breath analyzer constructed and operative according to a preferred embodiment of the present invention, to detect $^{13}CO_2$ in the breath of patients after ingestion of $^{13}$C-labeled urea, for the detection of *Helicobacter pylori* in the upper gastric tract. In the graphs shown, a value of 5 is chosen as the delta-over-baseline level to define a positive result. Patient number 1 thus has a negative result. Patients 2 and 3 show similar measurement curves, and it can be established after about 3 minutes that both of them have positive results. Patient number 4 has such a strong reaction to the ingest of the isotopically labeled substance that it becomes possible to provide a positive indication about his medical condition within 1 minute, and if the derivative method is used, in even less time.

The breath analyzer as proposed in the present invention is also operable in a number of different test modes, each with its own software package, for performing any breath test in which the patient ingests an isotopically labeled substance which produce isotopically labeled by-products detectable in the patients breath. Examples of a number of such breath tests are mentioned in the Background to the Invention section above.

It is clear that in all of the above preferred modes of operation, that the present invention provides a number of significant advantages over measurement procedures using previously available breath analyzers. Firstly, the exhaled breath of the subject can be analyzed in real time, so that there is relatively little delay between the time the specific gastro-intestinal reaction with the isotopically labeled substance takes place, and the time such activity is measured. Secondly, the samples of exhaled breath are obtained rapidly and are analyzed immediately in a manner which substantially increases the accuracy of the results. Thirdly, since multiple samples are obtained, the accuracy of the test is increased. Fourthly, there is less statistical error, since many samples are collected before a positive conclusion is reached. Fifthly, since samples are preferably collected until a preset level of accuracy is reached, ambiguous results can be substantially eliminated, preventing the need for repeat testing. Sixthly, since the analyzer itself makes the decision as to when sufficient samples have been analyzed to provide a clear indication of a medical condition, physiological differences between the response of different people to the various breath tests may be compensated for.

A further significant advantage of the use of the breath analyzer described in the present invention is that it increases patient compliance to a level that makes preventive medicine test procedures very acceptable. Furthermore, because of the considerably reduced costs of these tests, mass screening programs for a number of common gastro-enterological disorders could become more acceptable to health authorities and hence more widespread.

It will be appreciated by persons skilled in the art that the present invention is not limited by what has been particularly shown and described hereinabove. Rather the scope of the present invention includes both combinations and sub-combinations of various features described hereinabove as well as variations and modifications thereto which would occur to a person of skill in the art upon reading the above description and which are not in the prior art.

We claim:

1. A method of breath testing in which samples collected from exhaled breaths of a subject are analyzed by means of an analyzer, for a product of an isotopically labeled substance ingested by said subject, and comprising the steps of:

performing a first analyzing of a first sample collected from at least a first exhaled breath of said subject;

performing a second analyzing of a second sample collected from at least a second exhaled breath of said subject, at least said second sample being collected following the subject's ingestion of said substance; and providing an indication of a change in the level of said isotope labeled product in said second sample, while said subject is coupled to said analyzer.

2. The method of claim 1 wherein at least one of said first sample collected from at least a first exhaled breath of a subject and said sample collected from at least a second exhaled breath of said subject is at least one essentially complete exhaled breath of said subject.

3. The method of claim 1, wherein the first sample is collected prior to the subject's ingestion of the isotopically labeled substance, and the second sample is collected following the subject's ingestion of said isotopically labeled substance.

4. The method of claim 1, wherein both the first and second samples are collected following the subject's ingestion of said isotopically labeled substance.

5. The method of claim 1, wherein said second sample is exhaled following analysis of said first sample.

6. The method of claim 1, and further comprising the step of coupling the subject to the analyzer substantially continuously from the analyzing of said first sample to the analyzing of said second sample.

7. The method of claim 1, and further comprising the step of coupling the subject to the analyzer substantially continuously from the collection of said first sample to the collection of said second sample.

8. The method of claim 1, wherein the subject is coupled to said analyzer by means of a nasal cannula.

9. The method of claim 1, wherein the first analyzing of said subject's exhaled breath takes place prior to said product being detectable in said subject's breath and the second analyzing of said subject's exhaled breath takes place once said product could be detectable in said subject's breath.

10. The method of claim 1, and further comprising the step of determining that said test has a clinically significant outcome in accordance with the results of the ongoing analyses of said samples.

11. The method of claim 1, characterized in that said samples are collected by means of a nasal cannula.

12. The method of claim 1 and further comprising the steps of:
    fitting the results of the analyzing of successive samples to a curve; and
    determining from said curve whether said test has a clinically significant outcome.

13. The method of claim 12 wherein the derivative of said curve is used for said determining.

14. The method of claim 1, wherein the collection of said samples is discontinued according to the results of the ongoing analyses of said samples.

15. The method of claim 1, wherein the analyzing of said samples is discontinued according to the results of the ongoing analyses of said samples.

16. A method of breath testing comprising the steps of:
    collecting samples of a subject's exhaled breath substantially continually;
    analyzing said samples of a subject's exhaled breath for a product of an isotope labeled substance ingested by said subject; and
    providing an indication of the outcome of said analyzing in accordance with the results of the ongoing analyses of said breaths.

17. The method of claim 16 wherein said analyzing is performed substantially continually.

18. The method of claim 17, wherein the step of providing an indication of the outcome of said analyzing comprises the step of determining changes in an isotopic ratio in said samples of exhaled breath.

19. The method of claim 17, wherein said samples of exhaled breath are substantially every successive breath.

20. The method of claim 17, wherein said samples of exhaled breath are frequent samples of collected breath.

21. The method of claim 17, and further comprising the step of coupling the subject to the analyzer.

22. The method of claim 21, wherein the step of coupling the subject to said analyzer comprises the step of coupling the subject to said analyzer by means of a nasal cannula.

23. The method of claim 17 and further comprising the steps of:
    fitting the results of the analyzing of successive samples to a curve; and
    determining from said curve whether said test has a clinically significant outcome.

24. The method of claim 17, wherein the collection of said samples is discontinued according to the results of the ongoing analyses of said samples.

25. The method of claim 17, wherein the analyzing of said samples is discontinued according to the results of the ongoing analyses of said samples.

26. The method of claim 16, wherein the step of providing an indication of the outcome of said analyzing comprises the step of determining changes in an isotopic ratio in said samples of exhaled breath.

27. The method of claim 16, wherein said samples of exhaled breath are substantially every successive breath.

28. The method of claim 16, wherein said samples of exhaled breath are frequent samples of collected breath.

29. The method of claim 16, and further comprising the step of coupling the subject to the analyzer.

30. The method of claim 29, wherein the step of coupling the subject to said analyzer comprises the step of coupling the subject to said analyzer by means of a nasal cannula.

31. The method of claim 16 and further comprising the steps of:
    fitting the results of the analyzing of successive samples to a curve; and
    determining from said curve whether said test has a clinically significant outcome.

32. The method of claim 31 wherein the derivative of said curve is used for said determining.

33. The method of claim 16, wherein the collection of said samples is discontinued according to the results of the ongoing analyses of said samples.

34. The method of claim 16, wherein the analyzing of said samples is discontinued according to the results of the ongoing analyses of said samples.

35. A breath test analyzer which substantially continually collects samples of a subject's exhaled breath for analysis for a product of an isotope labeled substance ingested by said subject, and determines that said test has a clinically significant outcome in accordance with the results of the ongoing analyses of said samples.

36. A breath test analyzer according to claim 35 and comprising:
    a breath analysis chamber;
    a breath inlet conduit for conveying said exhaled breath from said subject to said breath analysis chamber; and
    a gas analyzer operative to analyze gas in said breath analysis chamber and to conduct a first analyzing of a first sample collected from at least a first exhaled breath of said subject, and a second analyzing of a second sample collected from at least a second exhaled breath of said subject, at least said second breath being collected following ingestion by the subject of said isotope labeled substance.

37. A breath test analyzer according to claim 36, wherein at least one of said first sample collected from at least first exhaled breath of a subject and said second sample collected from at least a second exhaled breath of said subject is at least one essentially complete exhaled breath of said subject.

38. A breath test analyzer according to claim 36, wherein the first sample is collected prior to the subject's ingestion of the isotopically labeled substance, and the second sample is collected following the subject's ingestion of said isotopically labeled substance.

39. A breath test analyzer according to claim 36, wherein both the first and the second samples are collected following the subject's ingestion of said isotopically labeled substance.

40. A breath test analyzer according to claim 36, wherein said second sample is exhaled following analysis of said first sample.

41. A breath test analyzer according to claim 36 and further comprising a breath collection chamber and a gas conduit for conveying a sample of gas from said breath collection chamber to said breath analysis chamber.

42. A breath test analyzer according to claim 41, wherein said breath analysis chamber and said breath collection chamber are combined, such that the analyzing of said samples takes place within said breath collection chamber.

43. A breath test analyzer according to claim 36, and wherein said gas analyzer comprises a gas discharge tube gas analyzer.

44. A breath test analyzer according to claim 36, and wherein said gas analyzer comprises an infra-red source which emits a discontinuous spectrum.

45. A breath test analyzer which analyses a first sample collected from at least a first exhaled breath of a subject and a second sample collected from at least a second exhaled breath of said subject for a product of an isotope labeled substance ingested by said subject, while the subject is coupled to the breath test analyzer.

46. A breath test analyzer according to claim 45, and comprising:
- a breath collection chamber;
- a breath analysis chamber;
- a breath inlet conduit for conveying said exhaled breath from said subject to said breath collection chamber;
- a gas conduit for conveying a sample of gas from said breath collection chamber to said breath analysis chamber; and
- a gas analyzer to analyze gas in said breath analysis chamber for said product of said isotope labeled substance ingested by said subject.

47. A breath test analyzer according to claim 46, wherein at least one of said first sample collected from at least a first exhaled breath of a subject and said second sample collected from at least a second exhaled breath of said subject is at least one essentially complete exhaled breath of said subject.

48. A breath test analyzer according to claim 46, wherein the first sample is collected prior to the subject's ingestion of the isotopically labeled substance, and the second sample is collected following the subject's ingestion of said isotopically labeled substance.

49. A breath test analyzer according to claim 46, wherein both the first and the second samples are collected following the subject's ingestion of said isotopically labeled substance.

50. A breath test analyzer according to claim 46, wherein said second sample is exhaled following analysis of said first sample.

51. A breath test analyzer according to claim 46, wherein said breath analysis chamber and said breath collection chamber are combined, such that the analyzing of said sample of gas takes place within said breath collection chamber.

52. A breath test analyzer according to claim 46, and wherein said gas analyzer comprises a gas discharge tube gas analyzer.

53. A breath test analyzer according to claim 46, and wherein said gas analyzer comprises an infra-red source which emits a discontinuous spectrum.

* * * * *